United States Patent [19]

Kitazume et al.

[11] Patent Number: 4,929,760
[45] Date of Patent: May 29, 1990

[54] FLUORINE-CONTAINING CARBONYL COMPOUNDS AND METHOD FOR PREPARING THE SAME

[75] Inventors: Tomoya Kitazume, Tokyo; Takashi Yamazaki, Kanagawa; Seiten Rin, Tokyo, all of Japan

[73] Assignee: Showa Shell Sekiyu Kabushiki Kaisha, Tokyo, Japan

[21] Appl. No.: 221,371

[22] Filed: Jul. 19, 1988

[30] Foreign Application Priority Data

Nov. 24, 1987 [JP] Japan .................. 62-294195
Nov. 24, 1987 [JP] Japan .................. 62-294196

[51] Int. Cl.$^5$ .................................... C07C 49/167
[52] U.S. Cl. .................. 568/308; 568/336; 568/416
[58] Field of Search ................. 568/416, 308, 336

[56] References Cited

U.S. PATENT DOCUMENTS

| 3,395,235 | 7/1968 | Litt | 568/308 |
| 3,764,274 | 10/1973 | Lucid | 568/308 |
| 4,067,884 | 1/1978 | Martini | 568/416 |

OTHER PUBLICATIONS

Kiehlmann et al., Can. J. Chem., vol. 51, pp. 3177–3181, 1973.
Lin et al., J. Org. Chem., vol. 52, pp. 3211–3217 (1987).
Solladie-Cavallo et al., Comm., vol. 1985, pp. 659–663.
Solladie-Cavallo et al., Tit. Letters, vol. 25, pp. 4117–4120 (1984).
Hanyawa et al., Chem. Pharm. Bull., vol. 35, pp. 1633–1636 (1987).

*Primary Examiner*—James H. Reamer
*Attorney, Agent, or Firm*—Darby & Darby

[57] ABSTRACT

Fluorine-containing carbonyl compounds of the formula

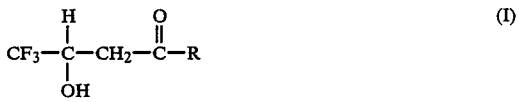

and its optically active isomers, which are useful for liquid crystal, bioactive substances, medicines, agricultural medicines such as fungicides, herbicides and hormones, organic functional materials and LB membranes, prepared by the reaction with trifluoro acetoaldehyde and RCOCH$_3$, wherein R is a substituted or not-substituted lower alkyl group, preferably a lower alkyl having not more than 10 carbon atoms, a substituted or not-substituted aromatic group or a substituted or not-substituted arylalkyl group.

13 Claims, No Drawings

FLUORINE-CONTAINING CARBONYL COMPOUNDS AND METHOD FOR PREPARING THE SAME

Application field of fluorine chemistry is becoming broader due to specific and unique properties of fluorine atom-containing compounds. There are many reports on bioactive materials having fluorine atoms in their molecules. In this field, an issue is mainly directed to relation between activity and molecular structure of a compound.

Synthesis of artificial organic fluorine compounds is very difficult, particularly in the case where fluorine atom or a trifluoromethyl group is introduced to asymmetric carbon in a molecule of a naturally produced, bioactive hydrocarbon substance.

This would possibly owe to the fact that fluorine atom introduced, even if only one, brings about great change in chemical properties of a molecule. Methods familiar to the skilled in the organic synthesis are hardly applied thereto without any modification.

Asymmetric hydrolysis of organic fluorine compounds is needed in order to use them as bioactive substances. No report has been found with respect to synthesis of optically active substances by use of microorganisms through asymmetric hydrolysis of fluorine compounds, particularly trifluoromethyl group-containing compounds, although there are numerous reports on synthesis of useful optically active compounds by asymmetric hydrolysis using enzymes obtained from microogranisms or animals.

It is important to develop an economical method which is able to have fluorine atoms introduced into the desired position in a molecule, while its configuration is controlled. However, as far as fluorine chemistry is concerned, neither a method for preparing both enantiomers or syn- and anti-diastereomers, controlling configuration, nor identification of absolute structure of the compound has been studied.

The present invention relates to compounds containing fluorine atoms in molecule thereof, more particularly, fluorine-containing carbonyl compounds and synthesis thereof and furthermore to asymmetric hydrolysis of esters of fluorine-containing carbonyl compounds by use of enzymes and the resulting optically active, fluorine-containing carbonyl compounds obtained therefrom. The present fluorine-containing carbonyl compounds are useful for liquid crystals, bioactive substances, medicines, agricultural medicines such as fungicides, herbicides and hormons, organic functional materials and LB membranes.

A racemic fluorine-containing carbonyl compound, one of the present compounds, has the formula of

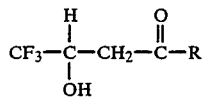   (I)

wherein R is a substituted or not-substituted lower alkyl group, preferably a lower alkyl having not more than 10 carbon atoms, a substituted or not-substituted aromatic group or a substituted or not-substituted arylalkyl gorup. R of the present compounds is, for instance, a phenyl group (Ph), a phenyulethyl group (CH₂CH₂Ph), an isobutyl group [CH₂CH(Me)₂] or a normal hexyl group [(CH₂)₅CH₃].

Synthesis of the Present Compounds

A fluorine-containing carbonyl compound having the formula (I) above is prepared by allowing trifluoroacetaldehyde to react with a compound of the formula

wherein R is the same as defined above, in the presence of lithium diisopropylamine.

Optically active fluorine-containing carbonyl compound, one of the present compounds, has the formula:

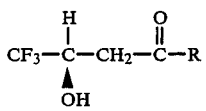

or

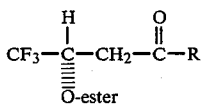

wherein R is the same as defined above.

Asymmetric Hydrolysis for Preparing the Optically Active Fluorine-Containing Carbonyl Compounds To buffer solution in which a hydrolase is suspended is added acetate of a racemic fluorine-containing carbonyl compound and the mixture is stirred for 6 hours.

After a flocculant is added, the mixture is further stirred for one hour. Hydrochloric acid is added until the mixture is acidified and precipitate produced is filtered off and an oily substance is extracted with diethyl ether. The products are separated by column chromatography (eluent: n-hexane-diethyl ether) to obtain the desired (R)-(+) alcohol from (S)-(−) ester. Hydrolysis of the (S)-(−) ester by use of a chemical procedure with aqueous alkaline solution or a biochemical procedure with cellulase provides (S)-(−) alochol without any racemization.

Lipase usable in the present invention is shown in the following table 1.

TABLE 1

| | Enzymes | Origins | Suppliers |
|---|---|---|---|
| 1 | Lipase MAPIO | Mucor sp. | Amano Seiyaku |
| 2 | Lipase MY | Candida cylindracea | Meito Sangyo |
| 3 | Lipase PL 679 | Alcaligenes sp. | " |
| 4 | Olipase 4S | Rizopus japonicus | Osaka Saikin Kenkyusho |
| 5 | Lipase "Saiken" 100 | " | Osaka Saikin Kenkyusho |
| 6 | Lipase | Rizopus niveus | Nagase Sangyo |
| 7 | Lipase | Rizopus delemar | Seikagaku Kogyo |
| 8 | Lipase T | Rizopus sp. | Carbio Chem. |
| 9 | Lipase TG | " | " |
| 10 | Lipase Godo BSL | Arthrobacter sp. | Godo Shusei |

The present invention is further explained by the following non-limitative examples.

EXAMPLE 1

Synthesis of 3,3,3-trifluoro-2-hydroxypropyl phenyl ketone

Dried tetrahydrofuran (50 ml) and dried lithium diisopropylamine (56 mmol) were charged into a flask under an argon atmosphere. The flask was cooled to −50° C. and thereto was added solution of acetophenone (6.0 g, 50 mmol) in dried tetrahydrofuran (10 ml).

The solution was stirred for 30 minutes at −50° C. and trifluoroacetaldehyde was bubbled thereinto. The solution was allowed to stand for 2 hours at 0° C.

Saturated aqueous ammonium chloride solution was added to the reaction solution. An oily material produced was extracted with diethyl ether and then the solvent was removed. A crude product was purified by silica gel chromatography [eluent=hexane:ethyl acetate=5:1 (vol.)] to obtain the titled compound. Yield:50%.

Proportion of the compound are $^{19}F$ NMR (CDCl$_3$)δ+2.0(d, $J_{CF_3-CH}$=7H2): $^1$NMR(CDCl$_3$)δ3.1(CH$_A$H$_B$, dd, $J_{HA-HB}$=34Hz, $J_{HA-CH}$=7.1Hz), 3.4(CH$_A$H$_B$, dd, $J_{HB-CH}$=14.1Hz), 4.1(OH, br), 4.63(CH, m), 7.43-7.93(Ar-H); IR(cm$^{-1}$) 3400(OH), 1685(C=0).

EXAMPLE 2

Synthesis of (3,3,3-trifluoro-2-hydroxy)propyl phenylethyl ketone, (3,3,3-trifluoror-2-hydroxy)propyl isobutyl ketone and (3,3,3-trifluoro-2-hydroxy)propyl n-hexyl ketone The procedure of example 1 was repeated except that (a) methylphenyl ethyl ketone (PhCH$_2$CH$_2$COCH$_3$), (b) methyl isobutyl ketone (CH$_3$)$_2$CHCH$_2$COCH$_3$ and (c) methyl n-hexyl ketone CH$_3$(CH$_2$)$_5$COCH$_3$ were used in place of the acetophenone (PhCOCH$_3$), respectively. Yields:50%, each.

Properties of these compounds and chemical shifts in $^{19}$F NMR, $^1$H NMR are shown in Table 2.

TABLE 2

| | $^{19}$F and $^1$H NMR Spectral data | | |
|---|---|---|---|
| | $^{19}$F NMR | | |
| Substrate | CF$_3$ | $J_{CF_3-CH}$, Hz | $^1$H NMR Chemical shift |
| CF$_3$CH(OH)CH$_2$C(O)Ph | 2.0 | 7.2 | 3.10(1H,dd), 3.40(1H,dd), 4.10(OH), 4.63(1H), 7.40-7.90(ArH) |
| CF$_3$CH(OH)CH$_2$C(O)CH$_2$CH$_2$Ph | 1.6 | 6.6 | 2.57-2.97(6H), 3.40(OH), 4.40(1H), 7.30-7.50(ArH) |
| CF$_3$CH(OH)CH$_2$C(O)CH$_2$CH(Me)$_2$ | 2.7 | 7.0 | 0.76(3H,d), 1.60-1.70(3H), 2.07(2H), 3.20(1H), 4.30(1H) |
| CF$_3$CH(OH)CH$_2$C(O)(CH$_2$)$_5$CH$_3$ | 2.0 | 6.5 | 0.93(3H,t), 1.43(8H), 2.47(2H), 2.73(2H), 3.78(OH), 4.43(1H) |

EXAMPLE 3

Synthesis of acetate derivative of 3,3,3-trifluoro-2-hydroxypropyl phenyl ketone Into a three-neck reduction flask containing methylene chloride (15 ml), 3,3,3-trifluoror-2-hydroxypropyl phenyl ketone (1.09 g, 5.00 mmol) was charged acetyl chloride (0.43 ml, 6.05 mmol) under a nitrogen atmosphere. The flask was cooled in an ice water bath. Pyridine (0.49 ml) was added to the flask drop by drop. The flask was left to stand at room temperature until temperature reached the room one and then the solution was stirred overnight.

After being quenched with 1H HCl, the reaction mixture was extracted with methylene chloride. The extract was washed with saturated aqueous sodium hydrogencarbonate. The extract was dried over anhydrous magnesium sulphate.

The solvent was distilled off under reduced pressure and the resulting residual liquid was purified by silica gel chromatography to obtain the titled acetate.

EXAMPLE 4

Asymmetric hydrolysis of acetate derivative of 3,3,3-trifluoro-2-hydroxypropyl phenyl ketone In buffer solution prepared from 1/15 M aqueous Na$_2$HPO$_3$ solution 946.1 ml) and 1/15 M aqueous KH$_2$PO$_4$ solution (13.9 ml) was suspended Lipase MY (Candida cylindracea, Meito Sangyo, 5 g). The solution was charged in a "Culstir" flask (100 ml, Shibata Kagaku) and was stirred for 15 minutes at 40°-41° C. Thereto was added 3,3,3-trifluoro-2-hydroxypropyl phenyl ketone acetate (200 mmol) synthesized in Example 1, and the mixture was stirred at 40°-41° C.

After 6 hours, "P-713" (200 ppm, 10 ml), a flocculant, produced by Daiichi Gokyo Seiyaku, was added drop by drop over a few minutes and the mixture was stirred for one hour. The mixture was acidified with 1N HCl until precipitate was produced. The precipitate was separated by filtration and an oily substance was extracted with ether. The ether layer was dried over anhydrous magnesium sulfate. After the ether was distilled off, the residual liquid was subjected to $^{19}$F-NMR assay (internal standard substance: C$_6$H$_5$-CF$_3$) in order to determine hydrolysis rate. (R)-(+)-3,3,3-trifluoro-2-hydroxypropyl phenyl ketone was purified by column chromatography on silica gel by using a mixture of n-hexane-diethyl ether (5:1).

Table 3 shows hydrolysis rate and optical purity.

EXAMPLE 5

Asymmetric hydrolysis of acetates of the following three 3,3,3-trifluoro-2-hydroxypropyl ketones CF$_3$CH(OH)CH$_2$C(O)CH$_2$CH$_2$Ph,
CF$_3$CH(OH)CH$_2$C(O)CH$_2$CH(Me)$_2$,
CF$_3$CH(OH)CH$_2$C(O)(CH$_2$)$_5$CH$_3$ The same procedure as in Example 4 was applied to the three compounds above to obtain the corresponding (R)-(+)-3,3,3-trifluoro-2-hydroxypropyl ketones.

Optical purity and hydrolysis rate are shown in Table 3.

TABLE 3

| | Optical resolution by use of Lipase MY | | | | |
|---|---|---|---|---|---|
| Compound | Rate of* hydrolysis | Hour h | [α]$_D$/MeOH, deg | Optical purity** % ee | Absolute configuration |
| CF$_3$CH(OH)CH$_2$C(O)Ph | 23 | 1 | +2.55 (c 1.69) | 92 | R |

TABLE 3-continued

| | Optical resolution by use of Lipase MY | | | | |
|---|---|---|---|---|---|
| Compound | Rate of* hydrolysis | Hour h | $[\alpha]_D$/MeOH, deg | Optical purity** % ee | Absolute configuration |
| CH$_3$CH(OH)CH$_2$C(O)CH$_2$CH$_2$Ph | 24 | 2 | +11.7 (c 0.84) | 91 | R |
| CF$_3$CH(OH)CH$_2$C(O)CH$_2$CH(Me)$_2$ | 28 | 1.5 | +14.0 (c 1.62) | 94 | R |
| CF$_3$CH(OH)CH$_2$C(O)(CH$_2$)$_5$CH$_3$ | 37 | 2 | +12.7 (c 2.06) | 90 | R |

Notes
*Calculated from $^{19}$F-NMR spectral strength.
**A mixture of (R)-(+)-3,3,3-trifluoro-2-hydroxy-propyl phenyl ketone (1 mmol) and (R)-α-methoxy-α-(trifluoromethyl)-phenyl acetic acid chloride (MTPA Cl) was stirred in pyridine (1 ml) at room temperature for 24 hours. The reaction mixture was poured into water and an oily substance produced was extracted with ether. The ether layer was washed with 1 N HCl, 5% NaHSO$_4$, saturated Na$_2$S$_2$O$_3$ and brine, in this order. After removal of the solvent, the diastereomeric ratio was determined by $^{19}$F-NMR signal intensity.

EXAMPLE 6

Hydrolysis of acetate derivative of (S)-(−)-3,3,3-trifluoro-2-hydroxypropyl phenyl ketone Suspension of Cellulase (3 g, manufactured by Yakuruto Yakuhin Kogyo) in the similar buffer solution (60 ml) to that used in Example 4 was charged in a "Culstir" flask (200 ml, manufactured by Shibata Kagaku). (S)-(−)-acetate (20 ml) of 3,3,3-trifluoro-2-hydroxypropyl phenyl ketone obtained in Example 4 was added thereto and the mixture was stirred at 40°–41° C. for 6 hours. Then, "P-713", a flocculant manufactured by Daiichi Kogyo Yakuhin (200 ppm in aqueous solution 10 ml) was added drop by drop over a few minutes and the mixture was stirred for one hour. The mixture was acidified with 1N HCl and precipitate produced was filtered off to obtain an oily substance.

After extraction of the oily substance with ether, drying and removal of the solvent, the residual liquid was chromatographed by silica gel [eluent=n-hexane:-diethyl ether=5:1 (vol)] to obtain (S)-(−)-3,3,3-trifluoro-2-hydroxypropyl phenyl ketone. Optical purity and hydrolysis rate of the resulting compound are shown in Table 4.

EXAMPLE 7

Chemical hydrolysis of acetate derivative of (S)-(−)-3,3,3-trifluoro-2-hydroxypropyl phenyl ketone A mixture of acetate (20 mmol) of (S)-(−)-3,3,3-trifluoror-2-hydroxypropyl phenyl ketone, aqueous sodium hydroxide solution (2 mol/l) and aceton (5 ml) was stirred at room temperature for 2 hours. The mixture was acidified with 1N HCl and precipitate produced was filtered off. After extraction of oily material was made with ether and drying, ether was distilled off. Crude product obtained was chromatographed by silica gel [eluent=n-hexane:diethyl ether=5:1 (vol)] to ogbtain (S)-(−)-3,3,3-trifluoro-2-hydroxypropyl phenyl ketone. Optical purity and hydrolysis rate of the resulting compound are shown in Table 4.

EXAMPLE 8

Hydrolysis of acetates of (S)-(−)-3,3,3-trifluoro-2-hydroxypropyl ketones of CF$_3$CH(OH)CH$_2$C(O)CH$_2$CH$_2$Ph, CF$_2$CH(OH)CH$_2$C(O)CH$_2$CH(Me)$_2$ and CF$_3$CH(OH)CH$_2$C(O)(CH$_2$)$_5$CH$_3$ The similar enzymatic or chemical procedures to Examples 6 and 7 were applied to the above compounds, to obtain the corresponding (S)-(−)-3,3,3-trifluoro-2-hydroxypropyl ketones. Optical purities and hydrolysis rates are shown in Table 4.

TABLE 4

| | Production of S-enantiomer | | | | |
|---|---|---|---|---|---|
| Compound | Yield % | Method* | Hour h | $[\alpha]_D$/MeOH deg | Optical purity % ee |
| CF$_3$CH(OH)CH$_2$C(O)CH$_2$CH$_2$Ph | 97 | B | 2 | −9.58 (c 2.52) | 75 |
| CF$_3$CH(OH)CH$_2$C(O)CH$_2$CH(Me)$_2$ | 93 | B | 3 | −12.7 (c 2.28) | 85 |
| CF$_3$CH(OH)CH$_2$C(O)CH$_2$CH(Me)$_2$** | 92 | B | 3 | −14.2 (c 1.87) | 94 |
| CF$_3$CH(OH)CH$_2$C(O)(CH$_2$)$_5$CH$_3$ | 97 | B | 2 | −9.34 (c 2.51) | 66 |
| CF$_3$CH(OH)CH$_2$C(O)(CH$_2$)$_5$CH$_3$** | 90 | B | 2 | −13.1 (c 1.45) | 93 |

Notes
*Hydrolysis of S-enantiomer acetate by cellulase.
**S acetate recovered from hydrolysis with lipase-MY (55–60% hydrolysis).

We claim:

1. Fluorine-containing carbonyl compounds of the formula

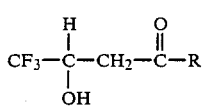

wherein R stands for a substituted or not-substituted C$_5$–C$_{10}$ alkyl group, a substituted or not-substituted aromatic group or a substituted or not-substituted arylalkyl group.

2. Optically active fluorine-containing compounds of the formula

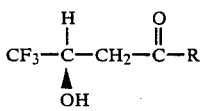

wherein R stands for a substituted or not-substituted lower alkyl group, a substituted or not-substituted aromatic group or a substituted or not-substituted arylalkyl group.

3. Optically active fluorine-containing compounds of the formula

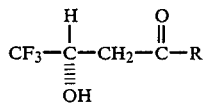

wherein R stands for a substituted or not-substituted lower alkyl group, a substituted or not-substituted aromatic group or a substituted or not-substituted arylalkyl group.

4. A compound in accordance with claim 1 wherein R is phenyl.

5. A compound in accordance with claim 1 wherein R is phenyl ethyl.

6. A compound in accordance with claim 1 wherein R is n-hexyl.

7. The compound of claim 4, R isomer.
8. The compound of claim 4, S isomer.
9. The compound of claim 5, R isomer.
10. The compound of claim 5, S isomer.
11. The compound of claim 6, R isomer.
12. The compound of claim 6, S isomer.
13. A compound selected from the group consisting of resolved R isomers and S isomers of compounds of the formula

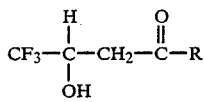

wherein R is ethyl or dimethyl ethyl.

* * * * *